US009409836B2

(12) United States Patent
Umbarkar et al.

(10) Patent No.: US 9,409,836 B2
(45) Date of Patent: Aug. 9, 2016

(54) PROCESS FOR HYDROGENATION OF OLEFINIC OR ACETYLENIC BONDS

(71) Applicant: Council of Scientific and Industrial Research, New Delhi (IN)

(72) Inventors: Shubhangi Bhalchandra Umbarkar, Pune (IN); Mohan Keraba Dongare, Pune (IN); Vaibhav Ravindrakumar Acham, Pune (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/374,148

(22) PCT Filed: Jan. 24, 2013

(86) PCT No.: PCT/IB2013/000076
§ 371 (c)(1),
(2) Date: Jul. 23, 2014

(87) PCT Pub. No.: WO2013/110995
PCT Pub. Date: Aug. 1, 2013

(65) Prior Publication Data
US 2015/0239821 A1    Aug. 27, 2015

(30) Foreign Application Priority Data

Jan. 25, 2012  (IN) .............................. 218/DEL/2012
May 4, 2012  (IN) ........................... 1361/DEL/2012

(51) Int. Cl.
*C07C 5/03* (2006.01)
*C07C 5/08* (2006.01)
(Continued)

(52) U.S. Cl.
CPC ................. *C07C 5/03* (2013.01); *B01J 23/002* (2013.01); *B01J 23/58* (2013.01); *B01J 23/6525* (2013.01);
(Continued)

(58) Field of Classification Search
CPC ............ B01J 23/58; B01J 23/44; B01J 23/88; B01J 23/652; B01J 23/002; C07C 5/03; C07C 5/08; C07C 5/09; C07C 5/02; C11C 3/126
See application file for complete search history.

(56) References Cited

U.S. PATENT DOCUMENTS

| 2,930,766 | A | * | 3/1960 | Lacey | ........................... 502/328 |
| 4,094,821 | A | * | 6/1978 | McVicker et al. | ............. 502/328 |
| 2012/0136176 | A1 | * | 5/2012 | Yamada et al. | ............... 568/459 |

FOREIGN PATENT DOCUMENTS

| GB | 814003 | * | 5/1959 |
| GB | 1033414 A | * | 6/1966 |

(Continued)

OTHER PUBLICATIONS

"International Application No. PCT/IB2013/000076, Article 34 Amendment mailed Jan. 30, 2014", (Jan. 30, 2014), 11 pgs.

(Continued)

*Primary Examiner* — Yate K Cutliff
(74) *Attorney, Agent, or Firm* — Schwegman, Lundberg & Woessner, P.A.

(57) ABSTRACT

The present invention relates to a process for hydrogenation of olefinic or acetylenic bonds. Further, the present invention relates to a process for selective hydrogenation of olefinic or acetylenic bonds and/including triglycerides using modified metal supported on solid acidic metal oxide catalyst and the process for the preparation thereof. The present invention provides a process for hydrogenation of olefinic or acetylenic bonds using metal supported on solid acid metal oxide based catalyst, at moderate conditions. The present invention also relates to the preparation of metal supported on solid acid metal oxide based catalyst for hydrogenation reactions under mild conditions.

10 Claims, 1 Drawing Sheet

(51) Int. Cl.
*B01J 23/58* (2006.01)
*B01J 23/652* (2006.01)
*B01J 37/02* (2006.01)
*C07C 29/17* (2006.01)
*C07C 67/303* (2006.01)
*C07C 41/20* (2006.01)
*C07C 45/62* (2006.01)
*C07C 51/36* (2006.01)
*C07B 35/02* (2006.01)
*C11C 3/12* (2006.01)
*B01J 23/00* (2006.01)
*C07C 5/05* (2006.01)

(52) U.S. Cl.
CPC ............. *B01J 37/0201* (2013.01); *C07B 35/02* (2013.01); *C07C 5/05* (2013.01); *C07C 5/08* (2013.01); *C07C 29/17* (2013.01); *C07C 29/172* (2013.01); *C07C 29/175* (2013.01); *C07C 41/20* (2013.01); *C07C 45/62* (2013.01); *C07C 51/36* (2013.01); *C07C 67/303* (2013.01); *C11C 3/126* (2013.01); *B01J 2523/00* (2013.01); *C07C 2101/14* (2013.01); *C07C 2101/18* (2013.01); *C07C 2102/08* (2013.01); *C07C 2521/08* (2013.01); *C07C 2521/10* (2013.01); *C07C 2523/28* (2013.01); *C07C 2523/44* (2013.01); *C07C 2523/58* (2013.01); *C07C 2523/652* (2013.01); *C07C 2527/1206* (2013.01); *Y02P 20/52* (2015.11)

(56) References Cited

FOREIGN PATENT DOCUMENTS

WO  WO-2005/052093  6/2005
WO  WO-2013/110995  8/2013

OTHER PUBLICATIONS

"International Application No. PCT/IB2013/000076, International Search Report mailed Oct. 30, 2013", (Oct. 30, 2013), 6 pgs.

Fernandez, M. B, et al., "Hydrogenation of edible oil over Pd-Me/Al2O3 catalysts (Me = Mo, V and Pb)", Journal of Molecular Catalysis A: Chemical, 233(1-2), (May 24, 2005), 133-139.

Mahata, N., et al., "Phenol hydrogenation over palladium supported on magnesia: Relationship between catalyst structure and performance", Phys. Chem. Chem. Phys., 3(13), (2001), 2712-2719.

Nijhuis, T. A, et al., "Optimized palladium catalyst systems for the selective liquid-phase hydrogenation of functionalyzed alkynes", Applied Catalysis A: General, 238(2), (Jan. 20, 2003), 259-271.

* cited by examiner

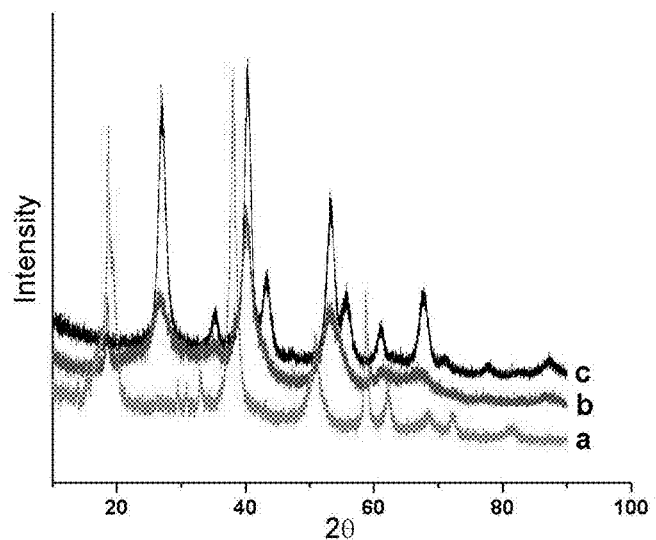

PROCESS FOR HYDROGENATION OF OLEFINIC OR ACETYLENIC BONDS

PRIORITY CLAIM TO RELATED APPLICATIONS

This application is a U.S. national stage application filed under 35 U.S.C. §371 from International Application Serial No. PCT/IB2013/000076, which was filed Jan. 24, 2013, and published as WO 2013/110995 on Aug. 1, 2013, and which claims priority to India Application No. 218/DEL/2012, filed Jan. 25, 2012, and to India Application No. 1361/DEL/2012, filed May 4, 2012, which applications and publication are incorporated by reference as if reproduced herein and made a part hereof in their entirety, and the benefit of priority of each of which is claimed herein.

TECHNICAL FIELD OF INVENTION

The present invention relates to a process for hydrogenation of olefinic or acetylenic bonds. Particularly, the present invention relates to a process for the selective hydrogenation of olefinic or acetylenic bonds using supported acidic metal oxide catalyst and the process for the preparation thereof. More particularly, the present invention provides a process for hydrogenation of olefinic or acetylenic bonds using metal supported on acidic metal oxide/modified acidic metal oxides at moderate conditions. The present invention also relates to the preparation of metal oxide based catalyst for hydrogenation reactions under mild conditions.

BACKGROUND AND PRIOR ART

Several catalysts have been tried for hydrogenation reactions. These catalysts are usually based on metals such as palladium, platinum and nickel supported on different oxides like silica, different carbon supports like carbon nanotubes, and charcoal as well as several polymers. Out of all these catalysts, palladium on charcoal is the most frequently used catalyst in industries and academia.

Though Pd/C is frequently used by the industry, it has some drawbacks such as pyrophoric nature when in contact with dry methanol. Normally hydrogenation reactions are carried out at melting temperature and high hydrogen pressure. Conventionally triglycerides and unsaturated fatty acids are hydrogenated using noble metal based catalysts or copper chromite or copper cadmium catalysts at melting temperature in the range of 150 to 250° C. and high hydrogen pressure. Specifically oils like castor oils are hydrogenated using nickel based catalysts at melting temperature (150-250° C.) and high pressure (up to 20 bar). Under these severe conditions, highly dispersed palladium or platinum particles sinter leading to loss of catalytic activity. Many times the noble metal loading in industrial catalyst varies from 1% to 10% of the support and higher loading leads to increase in the catalyst cost.

To overcome the severe reaction conditions and to evolve a cheaper catalyst for hydrogenation reactions is the need of the time.

OBJECT OF INVENTION

The main object of the present invention is to provide a process for hydrogenation of olefinic or acetylenic bonds.

Another object of the present invention is to provide a process for hydrogenation of olefinic or acetylenic bonds using modified acidic metal oxide catalyst and the process for the preparation thereof.

Another object of the present invention is to provide a simple, economical, efficient process for hydrogenation of olefinic or acetylenic bonds using metal oxide based catalyst or modified acidic metal oxide catalyst under mild conditions.

Another object of the invention is to provide a process for the preparation of metal oxide based supported catalyst for hydrogenation of olefinic and acetylenic bonds under mild conditions.

SUMMARY OF INVENTION

Accordingly, the present invention provides a process for hydrogenation of olefinic or acetylenic bonds, said process comprising:
a. activating a catalyst in a flow of hydrogen gas in a solvent 10 times volume of the substrate at room temperature ranging between 20-30° C.,
b. reacting the catalyst of step (a) with reactant in the range of 1-10 wt % with respect of substrate by stirring for 0.5-15 hours at atmospheric pressure and room temperature (20-30° C.),
c. obtaining the desired product from step (b), In an embodiment of the present invention the catalyst used in step (a) is solid acidic support comprising a metal oxide, mixed metal oxides or modified metal oxides.

In one embodiment of the present invention metals selected from group II A, IIIA, IVA, IB, IVB, VIB, and VIIIB.

In another embodiment of the present invention at least one elemental metal dispersed on said support wherein the elemental metal is selected from group VIB, IB or VIIIB metals in an amount up to 0.1-1.0 weight percent based upon the total weight of metal and support.

In yet another embodiment of the present invention yield and selectivity of desired product is up to 100%.

In yet another embodiment of the present invention the solvent is selected from toluene, methanol, and carbon tetra chloride.

In still another embodiment of the present invention a process for preparation of a catalyst for hydrogenation comprising:
a. preparing a slurry of solid acidic metal oxide, mixed metal oxides or modified metal oxides in water,
b. adding aqueous solution of elemental metal salt to solution of step (a) allowing water to evaporate to obtain the catalyst.

In still another embodiment of the present invention the acidity of the catalyst with modified magnesium oxide support ranges from 0.1-3.0 mmol/g of $NH_3$.

In still another embodiment of the present invention the specific surface area of the metal oxide based solid acid catalyst supports is in the range between 50 to 500 $m^2$/gm.

In still another embodiment of the present invention the specific acidity of the metal oxide based solid acid catalyst supports is in the range of 0.1 to 3.0 mmol/g of $NH_3$.

BRIEF DESCRIPTION OF FIGURE

FIG. 1: XRD patterns of palladium based magnesium fluorooxides.
  a) PMF (full form) 10: 1% palladium on magnesium oxide
  b) PMF11: 1% palladium on fluorinated magnesium oxide with Magnesium:Fluorine is 1:1
  c) PMF12: 1% palladium on fluorinated magnesium oxide with Magnesium:Fluorine is 1:2

DETAILED DESCRIPTION OF INVENTION

In the present invention a simple process for hydrogenation of olefinic and acetylene bonds using metal oxide based supported catalysts is disclosed.

In the invention selective hydrogenation of olefinic, acetylenic including edible and non edible triglycerides is carried out at room temperature (20-30° C.) and atmospheric pressure by bubbling hydrogen gas through the oil, using palladium based catalysts with up to 1% Pd loading on the acidic metal oxide support.

The catalyst of the invention comprises a metal selected from noble metals and metals from group VIIIB, IB and VIB. In a preferred embodiment of the invention the metals are selected from Ni, Cu, Cr, Pd, Pt, Rh, and Au. The metals of the invention have been uniformly dispersed on metal oxide based solid acid supports. The acidity of the catalyst ranges from 0.1-3.0 mmol/g of $NH_3$. Table 1 lists the different metal oxide based solid acid catalyst supports with specific surface area and specific acidity.

In the process of hydrogenation of olefinic and acetylenic bonds of the invention comprises:
  a. Activating the catalyst in a flow of hydrogen gas in a suitable solvent at room temperature, solvents preferably toluene, methanol, carbon tetra chloride;
  b. Reacting catalyst with reactant by stirring for 0.5-15 hours at atmospheric pressure and room temperature ranging from 20-35 deg C. and
  c. Obtaining the product of the process.

List of active metals supported on solid acidic support: Pd, Pt, Cu, Ni, Rh, Au, Cr

TABLE 1

Different metal oxide based solid acid catalyst supports with specific surface area and specific acidity.

| Sr. No. | Type of catalyst | Representative example | Range of Specific Surface area ($m^2/g$) | Range of Specific acidity (mmol/g $NH_3$) |
|---|---|---|---|---|
| 1 | Acidic Metal Oxides | Acidic alumina | 100-500 | 0.1-0.5 |
|  |  | Sulfted zirconia ($ZrO_2$—$SO_4$) | 100-500 | 0.1-0.6 |
| 2 | Mixed metal oxides | $MoO_3$—$SiO_2$ | 50-400 | 0.3-0.9 |
|  |  | $SiO_2/Al_2O_3$ | 300-700 | 0.2-0.4 |
|  |  | $TiO_2$—$SiO_2$ | 100-500 | 0.1-0.3 |
| 3 | Supported metal oxides | Heteropoly acids supported (HPW) on $SiO_2$ HPW = Silicotungstic acid, silicomolybdic acid, phosphomolybdic acid, phosphotungstic acid | 50-200 | 0.5 to 3.0 |
|  |  | Sn/MCM-41 | 200-1000 | 0.1-0.3 |
|  |  | $ZrO_2$—$B_2O_6$ | 50-180 | 0.2-0.5 |
| 4 | Acidic Zeolites | ZSM-5 | 400-450 | 0.3-2.5 |
|  |  | Y- type | 500-1000 | 0.3-2.5 |
| 5 | Clays | K-10 | 220-270 | 0.1-1.0 |
|  |  | Montmorillonite KSF | 20-40 | 0.1-1.0 |
| 6 | Acidic Resins | Amberlite IRS-120 | 1-20 | ~1 |
| 7 | Modified nietal oxides | $M_xO_y$ modified with aqueous HF; M = Mg, Ca, Sr, Ba, Al; X = 1, y = 1 or x = 2, y = 3 | 50-200 | 0.1-1.0 |

The process of hydrogenation of olefinic and acetylenic bonds is catalyzed by a novel modified magnesium oxide catalyst prepared by a process comprising:
  a. Preparing a slurry of magnesia in water;
  b. Adding aqueous solution of hydrogen fluoride to slurry of step (a) and stirred at room temperature for about an hour;
  c. Adding aqueous solution of a metal salt to suspension of step (b) with stirring and continued stirring for about 12 hours;
  d. Allowing water to evaporate to obtain modified acidic magnesium oxide catalyst The ratio of magnesium to fluoride varies from 1:0.1 to 1:2.

The modified magnesium oxide catalyst of the invention can be prepared replacing magnesium with calcium, strontium, barium or aluminium. The modified magnesium catalyst of the invention comprises a metal selected from noble metals and metals from group VIIIB, IB and VIB.

In the invention the metals are selected from Ni, Cu, Cr, Pd, Pt, Rh and Au.

In another aspect of the invention, the modified magnesium catalyst of the invention is characterized by XRD studies.

In the process of the invention, no leaching of palladium is observed and catalyst of the invention is recyclable.

The modified magnesium catalyst is used for catalysis for the process of hydrogenation of olefinic and acetylenic bonds as given in the following examples.

The metal oxide based catalyst may be further used for selective hydrogenation of olefinic double bonds under very mild conditions for various industrially important molecules including pharmaceuticals.

The invention can be better understood by the following non-limiting examples. The examples given are mere an illustration of the instant invention and should not be construed as limiting the scope of the present invention in any manner.

EXAMPLES

Example 1

The 50 mg 1% Pd-20% $MoO_3/SiO_2$ (impregnated) was activated for the period up to 0.5 h under the constant flow of hydrogen of 2 ml/min in the toluene (10 mL) with constant stirring at room temperature 27° C. To this solution 0.0.5 g styrene was added. The reaction was continued for 3 h. The samples were collected after specified time interval and analyzed by GC. The reaction was monitored by GC analysis. The products were confirmed by GC and GCMS analysis. In this reaction only product obtained was ethyl benzene with 100% conversion and >99.5% selectivity.

Example 2

The 50 mg 1% Pd-20% $MoO_3/SiO_2$ (impregnated) was activated for the period up to 0.5 h under the constant flow of hydrogen of 2 ml/min in the toluene (10 mL) with constant stirring at room temperature 27° C. To this solution 0.0.5 g Cinnamaldehyde was added. The reaction was continued for 3 h. The samples were collected after specified time interval and analyzed by GC. The reaction was monitored by GC analysis. The products were confirmed by GC and GCMS analysis. In this reaction only product obtained is 3-phenyl-propanol with >99% selectivity and 95% conversion.

Example 3

The 50 mg 1% Pd-20% $MoO_3/SiO_2$ (impregnated) was activated for the period up to 0.5 h under the constant flow of hydrogen of 2 ml/min in the methanol (10 mL) with constant stirring at room temperature 27° C. To this solution 0.5 g palm oil was added. The reaction was continued for 1.5 h. The samples were collected after specified time and analyzed by titration method by determination its Iodine value. At the end of reaction white solid was obtained which is palm wax (or hydrogenated palm oil) having Iodine value less than 12 and acid value up to 2 (same as that of the initial palm oil).

Example 4

The 50 mg 1% Pd-20% $MoO_3/SiO_2$ (impregnated) was activated for the period up to 0.5 h under the constant flow of hydrogen of 2 ml/min in the methanol (10 mL) with constant stirring at room temperature 27° C. To this solution 0.5 g castor oil was added. The reaction was continued for 1.5 h. The samples were collected after specified time and analyzed by titration method by determination its Iodine value. At the end of reaction white solid was obtained which castor wax (or hydrogenated castor oil) is having Iodine value around 14 and acid value up to 2 (same as that of the initial castor oil Example 5

The 50 mg 1% Pd-20% $MoO_3/SiO_2$ (impregnated) was activated for the period up to 0.5 h under the constant flow of hydrogen of 2 ml/min in the methanol (10 mL) with constant stirring at room temperature 27° C. To this solution was added 0.5 g oleic acid. The reaction was continued for 1 h. The samples were collected after specified time and analyzed by titration method by determination its Iodine value. At the end of reaction white solid was obtained which is stearic acid having Iodine value <1. The product was also confirmed by FTIR analysis which shows absence of double bond frequency.

Example 6

The 50 mg 1% Pd—$Al_2O_3$ (acidic) was activated for the period up to 0.5 h under the constant flow of hydrogen of 2 ml/min in the methanol (10 mL) with constant stirring at room temperature 27° C. To this solution 0.5 g castor oil was added. The reaction was continued for 6 h. The samples were collected after specified time and analyzed by titration method by determination its Iodine value. At the end of reaction white solid was obtained which is castor wax having Iodine value ~12 and acid value up to 2.

Example 7

The 50 mg 1% Pd-20% $MoO_3/SiO_2$ (impregnated) was activated for the period up to 0.5 h under the constant flow of hydrogen of 2 ml/min in the methanol (10 mL) with constant stirring at room temperature 27° C. To this solution 0.0.5 g castor oil was added. The reaction was continued for 3 h. The samples were collected after specified time and analyzed by titration method by determination its Iodine value. At the end of reaction white solid was obtained which is castor wax having Iodine value ~12 and acid value up to 2.

Example 8

The 50 mg 1% Pd-20% $MoO_3/SiO_2$ (sol gel) was activated for the period up to 0.5 h under the constant flow of hydrogen of 2 ml/min in the methanol (10 mL) with constant stirring at room, temperature 27° C. To this solution 0.5 g castor oil was added. The reaction was continued for 8 h. The samples were collected after specified time and analyzed by titration method by determination its Iodine value. At the end of reaction white solid was obtained which is castor wax having Iodine value ~30 and acid value up to 2.

Example 9

The 50 mg 1% Pd-resin (Amberlite IRS-120) was activated for the period up to 0.5 h under the constant flow of hydrogen of 2 ml/min in the methanol (10 mL) with constant stirring at room temperature 27° C. To this solution 0.0.5 g castor oil was added. The reaction was continued for 3 h. The samples were collected after specified time and analyzed by titration method by determination its Iodine value. At the end of reaction white solid was obtained which is castor wax having Iodine value ~15 and acid value up to 2.

Example 10

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.103 g, 1 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 11

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.052 g, 0.5 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 12

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.0102 g, 0.1 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 13

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.206 g, 2 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 14

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.515 g, 5 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 15

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.0206 g, 0.2 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 16

In 100 mL beaker, 4.0 g commercial magnesium oxide was added to 40 mL distilled water to form suspension at room temperature. This suspension was reacted with 10.0 mL aqueous hydrofluoric acid (commercial, 40%) with stirring at up to 1400 RPM. After the complete addition of hydrofluoric acid the reaction mixture was allowed to stir for 3 h. To this solution 5.0 mL acidic solution (1N HCl) of palladium chloride (0.031 g, 0.3 wt %) was added drop wise. The reaction mixture was kept under stirring for 16 h. The water was allowed to evaporate from the reaction by simply drying at 100° C. using hot plate with magnetic stirrer followed by heating at 150° C. in oven for 3 h. Catalyst yield was about 100%. Catalyst was characterized by PXRD.

Example 17

The 50 mg 1% Pd—MgO modified with HF as prepared in Example 10 was activated for the period up to 0.5 h under the constant flow of hydrogen of 2 mL/min in the toluene (10 mL) with constant stirring at room temperature 27° C. To this solution 0.0.5 g styrene was added. The reaction was continued for 3 h. The samples were collected after specified time interval and analyzed by GC. The reaction was monitored by GC analysis. The products were confirmed by GC and GCMS analysis. In this reaction only product obtained was ethyl benzene with 100% conversion and >99.5% selectivity.

Example 18

The 50 mg 1% Pd—MgO modified with HF as prepared in Example 10 was activated for the period up to 0.5 h under the constant flow of hydrogen of 2 mL/min in the methanol (10 ml) with constant stirring at temperature 27° C. To this solution 500 mg styrene was added. The reaction was continued for 3 h. The samples were collected after specified time interval and analyzed by GC. The reaction was monitored by GC analysis. The products were confirmed by GC and GCMS analysis. In this reaction only product obtained was ethyl benzene with 100% conversion and >99.5% selectivity.

Example 19

The 50 mg 1% Pd—MgO modified with HF as prepared in Example 10 was activated for the period up to 0.5 h under the constant flow of hydrogen of 2 mL/min in the toluene (10 mL) with constant stirring at room temperature 27° C. To this solution 0.5 g Cinnamldehyde was added. The reaction was continued for 3 h. The samples were collected after specified time interval and analyzed by GC. The reaction was monitored by GC analysis. The products were confirmed by GC and GCMS analysis. In this reaction only product obtained is 3-phenylpropanol with >99% selectivity and 95% conversion.

Example 20

The 50 mg 1% Pd—MgO modified with HF as prepared in Example 10 was activated for the period up to 0.5 h under the constant flow of hydrogen of 2 mL/min in the methanol (10 mL) with constant stirring at room temperature 27° C. To this solution was added 0.5 g palm oil. The reaction was continued for 1.5 h. The samples were collected after specified time and analyzed by titration method by determination its Iodine value. At the end of reaction white solid was obtained which is palm wax (or hydrogenated palm oil) having Iodine value <12 and acid value ~2 (same as that of the initial palm oil).

Example 21

The 50 mg 1% Pd—MgO modified with HF as prepared in Example 10 was activated for the period up to 0.5 h under the constant flow of hydrogen of 2 mL/min in the methanol (10 mL) with constant stirring at temperature 27° C. To this solution 0.5 g castor oil was added. The reaction was continued for 1.5 h. The samples were collected after specified time and analyzed by titration method for determination of iodine value. At the end of reaction white castor wax (or hydrogenated castor oil) with iodine value around 14 and acid value up to 2 (same as that of the initial castor oil) was obtained.

Example 22

The 50 mg 1% Pd—MgO modified with HF as prepared in Example 10 was activated for the period up to 0.5 h under the constant flow of hydrogen of 2 mL/min in the methanol (10 mL) with constant stirring at room temperature 27° C. To this solution 0.5 g oleic acid was added. The reaction was continued for 1 h. The samples were collected after specified time and analyzed by titration method by determination its Iodine value. At the end of reaction white solid was obtained which is stearic acid having Iodine value <1. The product was also confirmed by FTIR analysis which shows absence of double bond frequency.

Example 23-Example 38

Typical Procedure for Example 23 to Example 38

The 50 mg 1% Pd—MgO modified with HF as prepared in Example 10 was activated for the period up to 0.5 h under the constant flow of hydrogen of 10 mL/min in the methanol (10 mL) with constant stirring at mentioned temperature. To this solution was added 0.5 g of various substrates as given in table 2. The reaction was continued for specified time. The samples were collected intermittently and analyzed by GC and GCMS. The product was also confirmed by FTIR analysis which shows absence of olefinic C=C bond frequency. The reaction conditions and results are given in table 2.

TABLE 2

| Example | Substrate | Products | Time (h) | Temperature (° C.) | Conversion (%) | Selectivity (%) |
|---|---|---|---|---|---|---|
| 23 | cyclohexene | cyclohexane | 12 | RT | ~100 | 100 |
| 24 | Indene | Dihydroindene | 6 | RT | ~100 | 100 |
| 25 | Hexene | Hexane | 10 | RT | ~100 | 100 |
| 26 | Cyclooctene | Cyclooctane | 8 | RT | ~100 | 100 |
| 27 | α-Methylstyrene | Cumene | 12 | RT | ~100 | 100 |
| 28 | crotonaldehyde | Butanal | 9 | RT | ~100 | 99 |
| 29 | Cinnamyl alcohol | 3-phenyl propanol | 12 | RT | ~100 | 99 |
| 30 | Methyl acrylate | Methyl propanoate | 6 | RT | ~100 | 99 |
| 31 | Acrylic acid | Propionic acid | 5 | RT | 100 | 99 |
| 32 | Benzalaceto-phenone | 1,3-diphenyl-propanone | 6 | RT | 64.6 | 99 |
| 33 | But-2-yne-1,4-diol | 1,4-butandiol | 6 | RT | ~100 | 98 |
| 34 | cis-Stilbene | 1,2-diphenyl-ethane | 6 | 80 | 88.9 | 99 |
| 35 | trans-Stilbene | 1,2-diphenyl-ethane | 6 | 80 | 65.8 | 99 |
| 36 | 4-vinylanisole | 4-Ethylanisole | 6 | 80 | 95.0 | 99 |
| 37 | 2-Vinyl pyridine | Ethyl pyridine | 12 | 80 | 78.3 | 99 |
| 38 | Phenyl acetylene | Ethylbenzene | 6 | RT | 100 | 89 |

Example 39 to Example 52

General Procedure for Castor Oil Hydrogenation without Solvent at Melting Temperature and High Pressure A 50 mL high pressure autoclave was charged with 20.0 g of castor oil and required amount of catalyst from example 10 and hydrogen gas pressure 10 bar. The reaction mixture was stirred with 1800 RPM speed at required temperature. During the reaction the hydrogen gas pressure slowly decreased which was maintained using external gas pressure reservoir. The reaction was allowed to continue for the specific time. Once the reaction completed the product was separated from the catalyst and subjected for analysis. The white castor wax was analyzed using iodine value and melting point. The results are tabulated in table 3.

TABLE 3

Results of castor oil hydrogenation at high pressure and melting temprearure

| Example | Catalyst from Example | Catalyst (wt %) | Time (h) | Temperature (° C.) | Iodine Value | Melting point (° C.) |
|---|---|---|---|---|---|---|
| 39 | 10 | 10 | 3 | 60 | 10.8 | 71.8 |
| 40 | 10 | 5 | 3 | 60 | 12.7 | 80.2 |
| 41 | 10 | 3 | 3 | 60 | 29.2 | 80.2 |
| 42 | 10 | 4 | 5.30 | 90 | 9.5 | 81.9 |
| 43 | 10 | 5 | 2 | 100 | 30 | 72.9 |
| 44 | 10 | 3 | 2.40 | 100 | 29 | 76.9 |
| 45 | 14 | 3 | 1.30 | 100 | 4 | 82.0 |
| 46 | 15 | 5 | 8.30 | 100 | 32.27 | 68.4 |
| 47 | 14 | 5 | 2.25 | 100 | 15.6 | 69.4 |
| 48 | 16 | 5 | 3 | 100 | 45.04 | 73.1 |
| 49 | 14 | 3 | 2.5 | 100 | 31 | 66.4 |
| 50 | 10 | 5 | 3.15 | 100 | 22 | 80.5 |
| 51 | 14 | 3 | 4.30 | 100 | 66.6 | 59.0 |
| 52 | 14 | 3 | 1.50 | 100 | 33.29 | 79.1 |
| 53 | 16 | 5 | 6.0 | 80 | 17.16 | 78.1 |
| 54# | 10 | 10 | 3 | RT | 6.54 | — |
| 55@ | 10 | 10 | 4 | RT | — | 56.6 | with solvent methanol (1:10 oil:solvent),
@with solvent methanol (3:1 oil:solvent)

Example 56

Sunflower Oil Hydrogenation without Solvent at Room Temperature and High Pressure A 50 mL high pressure reactor charged with 20 g sunflower oil, 1 g catalyst from example 10 as prepared in example 10 and hydrogen gas pressure 10 bar. The reaction mixture was stirred with 1800 RPM speed at room temperature for 3 h. During the reaction the hydrogen gas pressure slowly decreased which was maintained using external gas pressure reservoir. Once the reaction was complete the product was separated from the catalyst and subjected for analysis. The iodine value of the white sunflower wax was found to be 56.

Example 57

Sunflower Oil Hydrogenation without Solvent at STP

A 50 mL high pressure autoclave was charged with 20 g sunflower oil 1 g catalyst from example 10 as prepared in example 10. Hydrogen gas was bubbled with 10 mL per min with constant stirring (1800 RPM speed) at room temperature for 7 h. The flow rate of hydrogen gas was kept constant by using external reservoir. Once the reaction was completed the product was separated from the catalyst and subjected for analysis. The iodine value of the white sunflower wax was found to be 64

Example 58

Rape Seed Oil Hydrogenation without Solvent at Melting Temperature and High Pressure A 50 mL high pressure autoclave was charged with 20 g rape seed oil, 1 g catalyst from example 10 and hydrogen gas pressure 10 bar. The reaction mixture was stirred with 1800 RPM speed at 100° C. for 3 h. During the reaction the hydrogen gas pressure slowly decreased which was maintained using external gas pressure reservoir. The reaction was allowed to continue for 6 h. Once the reaction was complete the product was separated from the catalyst and subjected for analysis. The iodine value and melting point of the whitish yellow rape seed wax was found to be 32 and 59° C. respectively.

Example 59

Rape Seed Fatty Acid Hydrogenation without Solvent at Melting Temperature and High Pressure A 50 mL high pressure autoclave was charged with 20 g rape seed fatty acid, 1 g catalyst from example 16, and hydrogen gas pressure 10 bar. The reaction mixture was stirred with 1800 RPM speed at 90° C. for 5 h. During the reaction the hydrogen gas pressure decreased slowly which was maintained using external gas pressure reservoir. The reaction was continued for 6 h. Once the reaction was complete the product was separated from the catalyst and subjected to analysis. The iodine value of the whitish saturated rape seed fatty acid was found to be 39. Also the partial reduction of olefinic double bond was confirmed by FTIR spectroscopy.

The advantages of the invention are:
1. Low metal loading—up to 0.1 wt %, hence lower cost of catalyst.
2. Room temperature hydrogenation at atmospheric pressure
3. Ease of operation.
4. No metal leaching.
5. Easily recyclable catalyst.
6. Environmentally benign process.
7. No pressure vessels are required hence low capital investment.
8. The hydrogenation using the present metal oxide based catalyst will be cheaper and safer compared to the conventional hydrogenation.

We claim:

1. A process for hydrogenation of olefinic or acetylenic bonds, said process comprising:
   a. activating a catalyst in a flow of hydrogen gas in a solvent 10 times volume of a reactant at room temperature ranging between 20-30° C.,
   b. reacting the catalyst of step (a) with the reactant of step (a) in the range of 1-10 wt % with respect to said reactant by stirring for 0.5-15 hours at atmospheric pressure and room temperature (20-30° C.) and
   c. obtaining the desired product from step (b), wherein said catalyst used in step (a) comprises an elemental metal or a metal salt supported on a solid acidic support comprising a metal oxide, mixed metal oxides or modified metal oxides, prepared by a process comprising:
      i. preparing a slurry of solid acidic metal oxide, mixed metal oxides or modified metal oxides in water,
      ii. adding an aqueous, acidic solution of elemental metal salt to solution of step (i), allowing water to evaporate to obtain the catalyst, and
      iii. heating the catalyst obtained in step (ii) at 150° C. for 3 h.

2. The process according to claim 1, wherein the metal in the metal oxide, mixed metal oxides or modified metal oxides are selected from group II A, IIIA, IVA, IB, IVB, VIB, and VIIIB.

3. The process according to claim 1, wherein at least one elemental metal is dispersed on said support, wherein the elemental metal is selected from group VIB, IB or VIIIB metals in an amount ranging from 0.1-1.0 weight percent based upon the total weight of metal and support.

4. The process according to claim 1, wherein yield and selectivity of desired product is up to 100%.

5. The process according to claim 1, wherein the solvent is selected from toluene, methanol, carbon tetra chloride.

6. The process according to claim 1, wherein the catalyst has a specific acidity and the specific acidity of a catalyst with a modified magnesium oxide support as the elemental metal or a metal salt supported on a solid acidic support comprising a metal oxide, mixed metal oxides or modified metal oxides ranges from 0.1-1.0 mmol/g of $NH_3$.

7. The process according to claim 1, wherein the metal oxide based solid acid catalyst support has a specific surface area in the range between 50 to 500 m2/gm.

8. The process according to claim 1, wherein the catalyst has a specific acidity and the specific acidity of a metal oxide based solid acid catalyst support as the elemental metal or a metal salt supported on a solid acidic support comprising a metal oxide, mixed metal oxides or modified metal oxides is in the range of 0.1 to 3.0 mmol/g of $NH_3$.

9. The process according to claim 1, wherein the acidic solution of elemental metal salt comprises an acidic solution of palladium chloride.

10. The process according to claim 1, wherein the acidic solution is added dropwise.

* * * * *